United States Patent [19]

Akiba et al.

[11] Patent Number: 5,209,275

[45] Date of Patent: May 11, 1993

[54] LIQUID DISPENSING APPARATUS AND METHOD BY SENSING THE TYPE OF LIQUID VAPORS IN THE RECEIVER

[75] Inventors: Jyuji Akiba, Iruma; Hiroyuki Sugibuchi, Tokorozawa; Kazuyuki Kojima, Sayama; Hiroshi Satoh, Iruma, all of Japan

[73] Assignee: Junkosha Co., Ltd., Tokyo, Japan

[21] Appl. No.: 751,317

[22] Filed: Aug. 28, 1991

Related U.S. Application Data

[63] Continuation of Ser. No. 427,253, Oct. 25, 1989, abandoned, which is a continuation-in-part of Ser. No. 210,100, Jun. 22, 1988, abandoned.

[30] Foreign Application Priority Data

Jul. 9, 1987 [JP] Japan .............................. 62-171808
Aug. 9, 1987 [JP] Japan .............................. 62-171807

[51] Int. Cl.$^5$ .......................................... G01N 27/46
[52] U.S. Cl. ...................................... 141/83; 141/192; 141/198; 141/95; 73/19.11; 73/23.2; 340/632; 204/431
[58] Field of Search ............... 141/83, 1, 94, 95, 96, 141/192, 198; 73/19.01, 23, 29, 19.1, 19.11; 338/22 SD, 34; 340/632; 422/90, 88; 204/431

[56] References Cited

U.S. PATENT DOCUMENTS

| | | | |
|---|---|---|---|
| 3,474,022 | 10/1969 | Culpepper et al. | 204/431 |
| 3,479,257 | 11/1969 | Shaver | 204/431 X |
| 3,493,484 | 2/1970 | Berg et al. | 204/431 |
| 3,658,479 | 4/1972 | Heijne et al. | 422/98 |
| 3,743,589 | 7/1973 | Nicholas | 204/431 |
| 3,981,181 | 9/1976 | Ochiai . | |
| 4,109,686 | 8/1978 | Phillips | 141/1 |
| 4,206,632 | 6/1980 | Suzuki . | |
| 4,247,299 | 1/1981 | Klein et al. | 422/98 X |
| 4,417,228 | 11/1983 | Takami et al. | 422/98 X |
| 4,469,149 | 9/1984 | Walkey et al. | 141/94 |
| 4,587,003 | 5/1986 | Tantrum et al. | 204/431 X |
| 4,608,232 | 8/1986 | Sunano et al. | 73/23 X |
| 4,631,952 | 12/1986 | Donaghey | 73/23 |
| 4,658,986 | 4/1987 | Freed et al. | 141/940 X |
| 4,663,614 | 5/1987 | Rauchwergen | 340/605 |
| 4,674,320 | 6/1987 | Hirschfeld | 73/23 |
| 4,761,639 | 8/1988 | Pyke et al. | 73/23 X |
| 4,838,323 | 6/1989 | Watts | 141/1 |

FOREIGN PATENT DOCUMENTS

| | | |
|---|---|---|
| 868415 | 10/1978 | Belgium . |
| 68747 | 1/1983 | European Pat. Off. . |
| 186039 | 2/1986 | European Pat. Off. . |
| 184062 | 6/1986 | European Pat. Off. . |
| 0246684 | 11/1987 | European Pat. Off. ............... 141/83 |
| 2502134 | 9/1982 | France .................................. 141/94 |
| 60-115901 | 6/1985 | Japan . |
| 60-209144 | 10/1985 | Japan . |
| 61-142609 | 6/1986 | Japan . |
| 62-208399 | 9/1987 | Japan . |
| 2277548 | 12/1987 | Japan .................................. 204/431 |
| 1294117 | 10/1972 | United Kingdom . |
| 1586751 | 3/1981 | United Kingdom . |

Primary Examiner—Ernest G. Cusick
Attorney, Agent, or Firm—Horst M. Kasper

[57] ABSTRACT

The invention relates to a liquid dispensing apparatus which includes a detecting element for detecting the liquid from the vaporized gas surrounding the remaining liquid in a storage tank to be supplied, where the detecting element is disposed at the output end of a liquid supply line, and a discriminator for discriminating the signals and information obtained from such a detecting element. The discriminator generates a lock signal to be fed to a locking means for allowing suspension of the supply of liquid based on a signal generated in the discriminator and fed to the locking means. The detection element includes a first electrode, a second electrode, a gas-sensing member connected to the first electrode and connected to the second electrode, which gas-sensing member is formed of a resin material including a conducting material which furnishes an impedance change upon contacting the vaporized gas of the liquid to be detected.

4 Claims, 5 Drawing Sheets

LIQUID DISPENSING APPARATUS AND METHOD BY SENSING THE TYPE OF LIQUID VAPORS IN THE RECEIVER

CROSS-REFERENCE TO RELATED APPLICATIONS

This application is a continuation application of application Ser. No. 427,253 filed Oct. 25, 1989, now abandoned, which is a continuation application filed Jun. 22, 1988 and bearing Ser. No. 07/210,100 abandoned. The entire disclosure of this latter application, including the drawings thereof, is hereby incorporated in this application as if fully set forth herein.

BACKGROUND OF THE INVENTION

1. Field of the Invention

The present invention relates to an apparatus for dispensing vaporizable liquids and an associated detecting element for vaporized liquid.

2. Brief Description of the Background of the Invention Including Prior Art

Petroleum, gasoline, or other vaporizable industrial liquids are in general accompanied by inherent dangers based on their properties, such as flammability. Furthermore, these liquids have to match the equipment which uses them. For this reason, it is important, prior to transferring such liquid to a supply tank, to confirm and to distinguish what kind of liquid is employed and to use an element suitable for distinguishing various kinds of vaporized liquids.

Vaporizable liquids have to be transferred under carefully monitored conditions and safety checks in order to prevent accidents in an industrial, commercial, and residential environment. It would be desirable to have an automatic check in order to save labor.

In this motorized age, in particular in the dispensing of diesel to passenger cars with diesel engines, there have occurred an increasing number of errors at motor-vehicle service stations, i.e. the pumping of gasoline by mistake in place of light oil.

Another problem is the occurrence of accidents caused by an erroneous supply of fuel to individual underground tanks, on the occasion of supplying different kinds and grades of fuel to sections provided in an underground tank for the convenience of fuel transfer to a gas-service station by a large-size tank truck.

Oil detection systems can be based on a detection of changes of the electrostatic capacitance of a line caused by penetration and permeation of liquid oil into a sensor formed by a coaxial cable, as is taught in the Japanese Patent Application Laid Open No. 61-142,609 and, alternatively, by an element which optically detects a liquid, such as oil, as is taught in the Japanese Patent Applications Laid Open Nos. 60-209,144 and 60-115,901. These teachings, however, are directed to the sensing of oil as a liquid and are therefore not suitable for detecting of leaked oil or vaporized liquids in the surroundings and input ports of an oil tank supply.

U.S. Pat. No. 4,838,323 to Andrew J. Watts teaches a system for preventing the accidental addition of automotive fuel to the fuel tank of a gasoline-fuelled vehicle at retail filling stations. A nozzle with sensor system is connected to a processor and the processor is connected to a display. When a diesel fuel tank is erroneously connected to a gasoline delivery pump, the pump will be disconnected if the value of the vapor pressure is below a predetermined value, which means the tank already contains diesel fuel.

SUMMARY OF THE INVENTION

1. Purposes of the Invention

It is an object of the present invention to provide a liquid supply apparatus which is capable of discriminating and distinguishing the kinds of liquid present in and to be supplied to an operating storage tank from a gas vaporized from the liquid remaining in such storage tank, where such storage tank requires additional supply.

It is a further object of the invention to provide a system which will only allow supply of liquid in cases where the remaining residual liquid in the storage tank, which requires additional supply, matches the kind of the liquid to be supplied, or which supply apparatus stops supply of liquid when there is no match between the kind of the liquid in the storage tank and the kind of the liquid in the supply line, in order to prevent accidents and in order to save labor by eliminating an individual, personal checking requirement.

It is another object of the invention to provide a sensor which can detect the kind or quality of a liquid within a short delay period of time, and which sensor initiates resetting for reuse, within another short period of time, after the oil or liquid dispense-preventing means, e.g. for a gasoline-service station, has attempted erroneously to service a non-matching tank and this provides additional safety for gasoline-service stations active in the dispensing of fuel to automobiles carrying diesel engines.

It is yet another object of the present invention to provide a vaporized-liquid detecting element and vaporized-liquid discrimination apparatus which are capable of detecting, within a short time period, the quality and the kind of oil and/or liquid, such as gasoline, light oil, and kerosene, and which can be reset for renewed sensing within a short time period.

These and other objects and advantages of the present invention will become evident from the description which follows.

2. Brief Description of the Invention

The present invention provides for a liquid dispensing apparatus which includes a detecting element for detecting the liquid from the vaporized gas surrounding the remaining liquid in a storage tank to be supplied. The detecting element is disposed at the output end of a liquid supply line and a discriminator discriminates the signals and information obtained from such a detecting element. The discriminator generates a lock signal to be fed to a locking means for allowing suspension of the supply of liquid based on a signal generated in the discriminator and fed to the locking means.

Such structure, where the detecting element is disposed at the outer surface of the output end of the liquid supply line, for example, at the external circumference of the end part of a liquid supply gun, the kind of the liquid in a liquid storage supply tank, requiring additional supply, can be detected accurately and it can be prevented that a liquid of a different quality and kind is added to said liquid storage tank. Accordingly, it is advantageous when such a detecting element can be used automatically without having to wait for a dry condition. Where the detecting element is furnished in the supply path of the liquid, such a detecting element is preferably provided with a film which is permeable to gases but which is impermeable to liquids. The locking means can efficiently utilize a sequential circuit, which stops and interrupts operation of a liquid supply pump. A valve body and/or a mechanical locking element can be stopped and can interrupt the ON condition of a switch for a motor and, in particular, for an electric motor driving an associated liquid supply pump.

Since the liquid, remaining in the storage tank to be resupplied, can be detected from the vaporized liquid in gas form, the detecting means can be formed in a simple way. It requires little time for performing the detection and it can be reset quickly to use at full detection condition. Furthermore, a precise discrimination can be realized depending on a timing element, such as a differentiation value or an integral value in the control system. In case of the liquid remaining in a storage tank, requiring additional supply, is matching a liquid to be supplied, then the liquid supply can be performed smoothly without actuation of a locking operation. However, if the liquid to be supplied does not match the residual liquid retained in the storage tank, which tank requires additional supply, the discriminator generates a locking signal based on information received from the detecting element and, consequently, the locking means is actuated for suspending and interrupting the supply of liquid to the storage tank to be replenished.

The detecting element can be protected from getting wet by the liquid to be supplied and can be immediately reused for the next detection situation by positioning it on an external surface or circumference of an output end of a liquid supply line, i.e. placing it on the outside of an end of a conduit used for passing the liquid.

According to a further aspect of the invention, a vaporized-liquid detecting element comprises a first electrode, a second electrode, a gas-sensing member disposed between the first and the second electrode, and which gas-sensing member is formed by a resin material including a conductive substance. The resin material of the gas-sensing member shows an impedance change when contact occurs with a gas vaporized from a liquid to be detected.

A detecting element bridges at least a pair of electrodes with a gas-sensing member which is formed of a resin material which includes a conductive material, where the conductivity depends on the gas vaporized from the liquid to be detected. A measuring means has an input connected to the detecting element and provides an output signal reflecting any impedance change of such detecting element, depending on such impedance change. A discriminating means has an input connected to an output of the measuring means and provides a function control signal, depending on and discriminating the liquid to be detected.

The vaporized-liquid detecting element can have a structure where at least a pair of electrodes are bridged by a gas-sensing member made of a resin material, including a conducting substance. Therefore, for example, molecules of an oil liquid, volatilized from an oil, penetrate into said gas-sensing member and surround the particles of a conductive substance, thereby inhibiting electrical conduction in the vaporized-liquid detecting element, and thereby changing or increasing the resistance or impedance value between the two electrodes. A measuring means has its input connected to the two electrodes for detecting the impedance of the gas-sensing member, and the output of the measuring means is transmitted to a discriminator. An increase in the impedance value has a positive correlation with the number of molecules of oil surrounding the particles of the conductive substance in the detecting member, and the increment associated with the presence of gasoline, having a high volatility, rises sharply in comparison with a rise associated with light oil or kerosene. A degree of volatility, which is different depending on the kind and quality of oil, shows a particular impedance value under constant conditions. Therefore, the kind and quality of oil and/or liquid can be discriminated by comparing the impedance value when the vaporized-liquid detecting element, preset at a calculated or empiric setpoint value, is placed in the ambience of the volatile gas, or by deciding whether such impedance value has exceeded the constant threshold value, or in accordance with a value such as an integral value or differential value, i.e. the rate of variation. Both the static and the dynamic qualities of the change of resistance of the detecting element can be employed in the safety-checking process.

A detecting element for detecting a vaporized liquid is an element which is suitable to interact with a vaporized liquid and for providing a signal indicating the kind and/or quality of such vaporized liquid. Such detecting elements can be based on various physical principles. A preferred element is based on the absorption properties of conductors, which are capable in changing their conductivity based on the amount and kind of the gaseous material absorbed. Preferably, such gaseous materials are discriminated by a membrane which is permeable to certain kinds of gases. Other detector elements could be based on different properties of gases, such as conductivity of gases, ionization of gases, viscosity of gases, thermal behavior of gases, and other properties.

A measurement means is a device which is suitable to be attached to a sensor and which can receive a signal from a sensor and provide an electrical output signal of a size and quality which is a direct representation of the sensor state and which is suitable for further processing in digital or analog circuits.

A discriminator is a device which is capable of comparing a signal received relative to preset signal values. Preferably, this is an electronic device which has stored in some memory element one or more preset signals and which is capable of comparing such a stored preset signal with an input of an actual signal and which performs a logic function comparing the incoming actual signal with a preset signal and provides an output based on such comparison. In particular, the discriminator should be capable of providing a lock signal, which can be further amplified in a final control element and which can serve to provide a mechanical motion and mechanical closure if such situation is determined based on the signals provided by the sensor.

The novel features which are considered as characteristic for the invention are set forth in the appended claims. The invention itself, however, both as to its construction and its method of operation, together with additional objects and advantages thereof, will be best understood from the following description of specific embodiments when read in connection with the accompanying drawing.

BRIEF DESCRIPTION OF THE DRAWING

In the accompanying drawing, in which are shown several of the various possible embodiments of the present invention.

DESCRIPTION OF INVENTION AND PREFERRED EMBODIMENT

Figure 1:
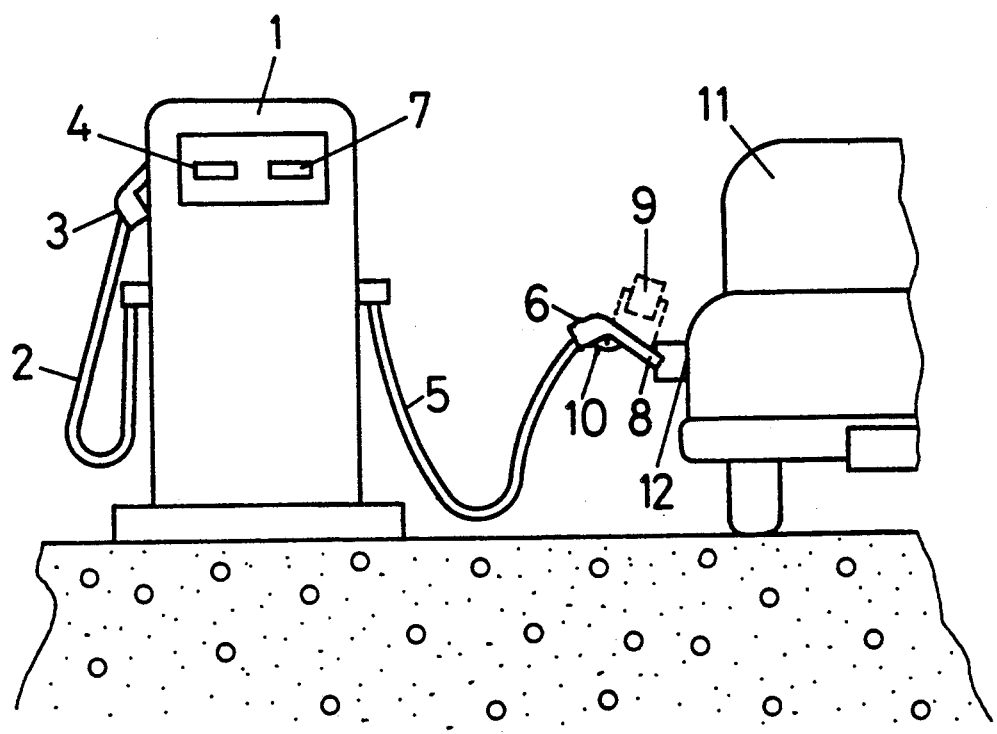
FIG. 1 is a schematic view of a gasoline-service station for dispensing gasoline to an automobile.

FIG. 1 illustrates schematically a gas-service station for dispensing gasoline to an automobile. In a pump-station 1 for a class two oil supply, there are disposed, on the left-hand side, a light-oil supply hose 2, a light-oil supply gun 3, and a light-oil meter 4 and, on the right-hand side, a gasoline supply hose 5, a gasoline supply gun 6, and a gasoline meter 7.

In accordance with the present invention, the gas-sensing detecting element 8 is provided to the external surface or circumference of the output end part of a light-oil supply gun 3 or to that of a gasoline supply gun 6, respectively. The gas-sensing detecting element can be at a distance from about 0.2 to 30 cm from the extreme end point of such supply gun and is preferably from about 1 to 10 cm from such extreme end part. This detecting element 8 utilizes, for example, as will be described in more detail below, a conductive polytetrafluoroethylene resin film, including a conductive member such as carbon black of 50 weight-percent as the gas-sensing part. This element exhibits excellent weather resistance properties. The detecting element 8 generates different information signals depending on the gas surrounding the element. This information is received and processed by the discriminator 9. If the discriminator determines that the liquid of the supply gun is different from the residual liquid present in a tank, the locking signal is generated and supplied to operate a locking means.

According to this embodiment, the supply of gasoline is interrupted and disabled by mechanically fixing a trigger 10 of the liquid supply guns 3, 6, depending on the signal generated by the discriminator 9. The locking means can also be capable of employing a sequential circuit which operates to interrupt the drive of an oil-supply pump, for example within the oil-dispensing pump station 1, or at another location. A valve body can be provided between the oil-supply lines to interrupt flow of liquids and gasolines.

Now, if a passenger car 11, having a diesel engine, enters a gasoline-service station and a service attendant unknowingly applies a gasoline-supply gu 6 to the supply port 12 of the passenger car, even though the passenger car requires a supply of light oil for internal combustion, then the detecting element 8, provided at the output end of the supply gun 6, detects the presence of vaporized light oil of the remaining fuel in the tank coming from the supply port 12. The discriminator 9 now provides a signal that, according to the information signal received from the detecting element 8, the supply of light oil is requested. Since the information received from the detecting element 8 is different from the information associated with the fuel of the supply line, a locking signal is generated. Based on the locking signal, the trigger 10 for supplying the liquid fuel is locked and the fuel cannot be supplied, thereby preventing a dispensing of the wrong fuel. Accordingly, the gasoline supply gun 6 is returned to and hooked up in the oil-dispensing pump station 1, and the light-oil supply gun 3 is then used to provide the light oil as required. In this case, since the discriminator 9, responding to the detecting element 8 provided at the outlet end of the light-oil supply gun 3, is preset to light oil, the locking signal is no longer activated and the light oil is properly dispensed to the passenger car 11.

Figure 2:
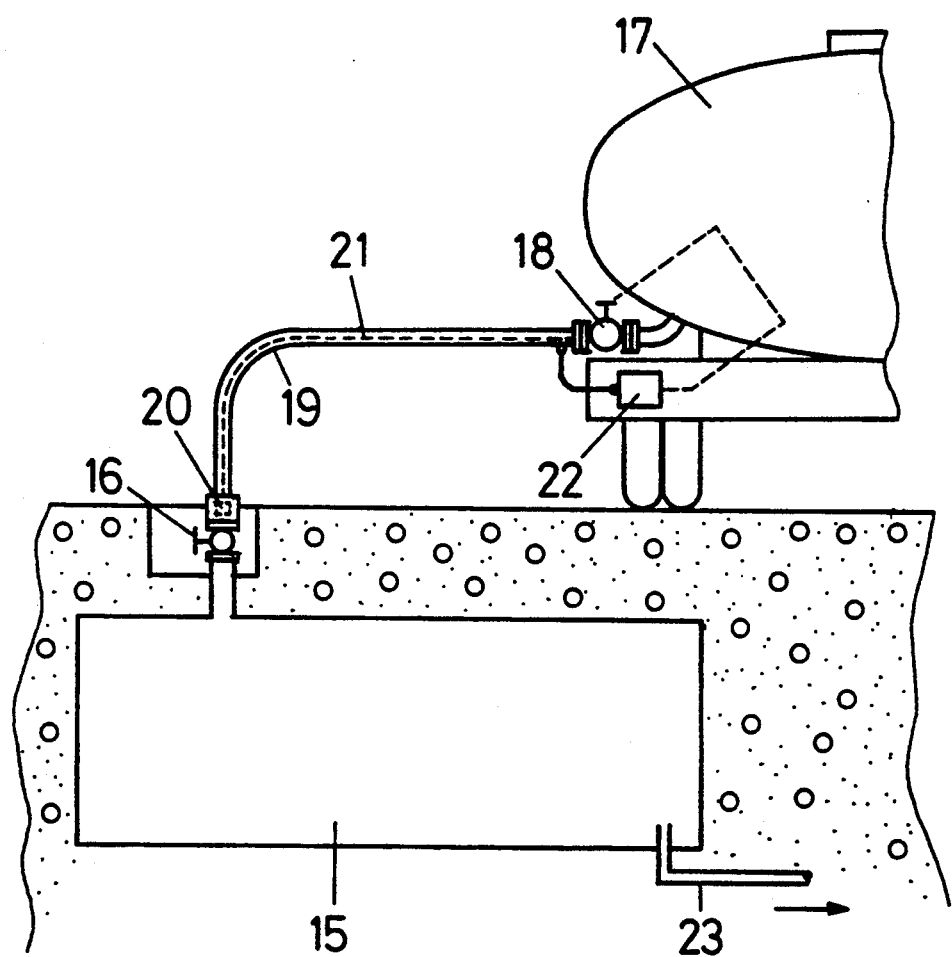
FIG. 2 is a second embodiment of the invention, illustrated schematically, providing an example of supplying oil from a tank truck to an underground tank of a gasoline-service station.

FIG. 2 is another embodiment of the invention illustrating an example of supplying oil to an underground tank of a gas-service station from a tank truck. The second end of a supply hose 19 is connected to the light-oil tank release valve 18 of the tank truck 17 and the first end of the supply hose 19 is connected with an oil supply valve 16 of an underground tank 15 for gasoline. If the oil supply valve 16 is now opened, the detecting element 20, protected by a film which is permeable to a gas but is impermeable to a liquid, and which is provided within the oil supply hose 19 at the second end, detects vaporized gas of gasoline within the underground tank 15. Thus, the discriminator 22, receiving information signals through a connection wire 21, running between the detecting element 20 and the discriminator 22, which is set for light oil, generates a locking signal causing interruption of the opening connection of the release valve 18.

Accordingly, an accident and an error in supplying light oil from the tank truck 17 to an underground tank 15 for gasoline and, vice versa, the dispensing of light oil from a gasoline supply post to a car, running on gasoline, can be prevented based on a properly prepared coupling line 23.

Figure 6:
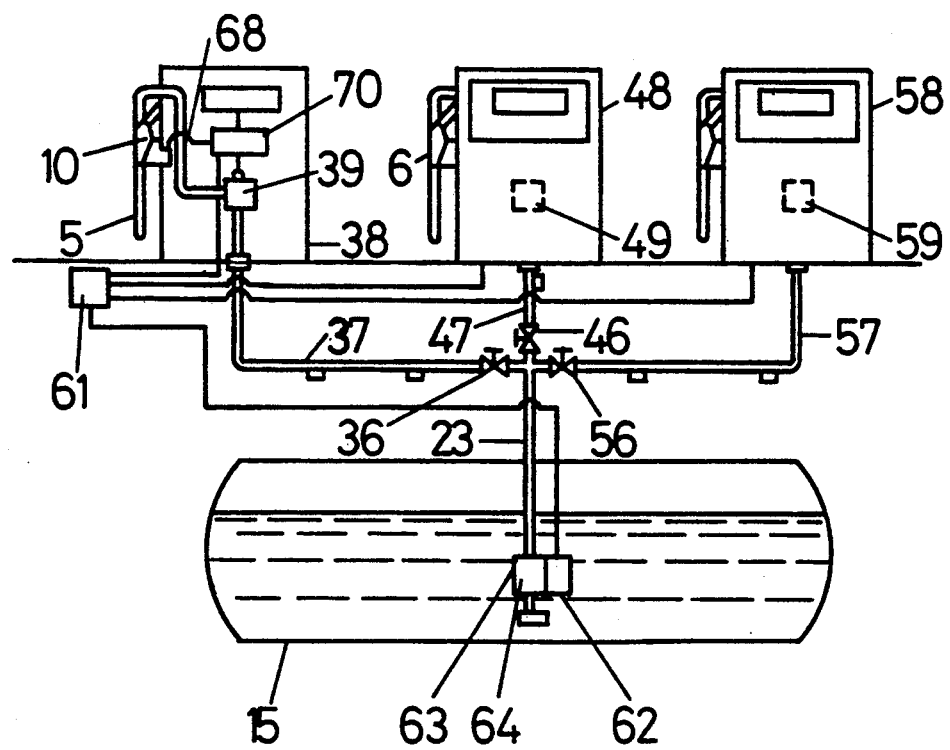
FIG. 6 is schematic diagram of a liquid supply pump employing the detecting element.

FIG. 6 illustrates in more detail the dispensing part and its connection to the storage tank 15 by a coupling line 23. The coupling line 23 connects to valves 36, 46 and 56 which in turn are connected via lines 37, 47, 57 to dispensing posts with pedestals 38, 48, 58. The dispensing posts with pedestals 38, 48 and 58 contain metering valves 39, 49, 59 for metering and distributing the gasoline. A switch box 61 is connected to the output triggers or output levers 20 attached to the dispenser nozzle 66 or to the metering valves 39, 49, 59. The metering valves 39, 49, and 59 are connected to respectively a liter or a gallon totalizer and to a respective money totalizer. An electrical conduit 68 connects the dispenser gun 6, holding the nozzle 66, to a control system 70 interposed between the metering valves 39, 49 and 59 and a respective money totalizer display and-/or volume totalizer display.

Figure 3:
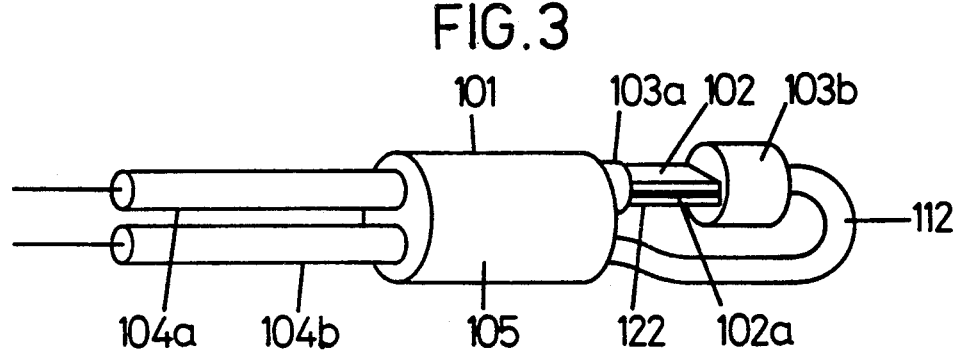
FIG. 3 is a schematic perspective view of a vaporized-liquid detecting element.

Referring now to FIG. 3, there is provided a sensor 102 which is connected with a lead wire 104a through the connecting part 103a at one end and with a lead wire 104b through a connecting part 103b at the other end. A pair of connection lead wires 104a, 104b is integrated through the outer sheath or jacket 105, which comprises a thermally contractable tube, where these items together form a vaporized-liquid detecting element 101.

The sensor 102 is now explained in further detail. First, extruded material is formed by adding and kneading a liquid lubricating agent or a softener of about 20 weight-percent to a mixture of carbon powder, such as carbon black of about 10 to 50 weight-percent, and the polytetrafluoroethylene, also called PTFE, resin powder are mixed, followed by molding of the mixture. The extruded material is expanded to about 1 to 15 times, at least in one direction, at a temperature of from about 300° to 350° C., and preferably from about 325° to 330° C., for forming a conductive tape. Thereafter, the polytetrafluoroethylene tape 122 is adhesively attached to both sides of the gas-sensing sensor part 102a for protection purposes. Unbaked, uncured, incompletely baked, or incompletely cured, solid polytetrafluoroethylene as well as unbaked, uncured, incompletely baked rolled, or incompletely cured rolled and extended porous polytetrafluoroethylene tape can be used for the conductive tape. In the context of this invention, incompletely baked or cured means that not more than 80 percent of the linkages of a completed baking or curing process have been formed. The polytetrafluoroethylene tape has a critical surface tension which is smaller than that of water but which is larger than that of oil. Preferably, the surface tension is at least about 10 percent higher than water and 10 percent lower than oil. Consequently, such a polytetrafluoroethylene tape 122 has the capability to repel water and to absorb molecules of a vaporized oil or liquid. Accordingly, when the vaporized-liquid detecting element 101 is placed into an ambience including oil, then the molecules of the vaporized oil pass through the polytetrafluoroethylene tape and then enter into the gas-sensing part 102a, and penetrate into the surface, and interfere with the electric conductivity, of carbon black particles forming the gas-sensing part 102a, thereby increasing the electric resistance and impedance of the gas-sensing part 102a of the detecting element 102.

Preferably, the lead terminals of the sensor 102 are disposed such that the detector extends in a direction parallel to the connecting wires, with one of the connecting wires making a reverse turn 112 for connecting to the measuring means 107. The connecting parts 103a and 103b can be made of plastic with bore holes for wires and a seating for the sensor 102.

Figure 5:
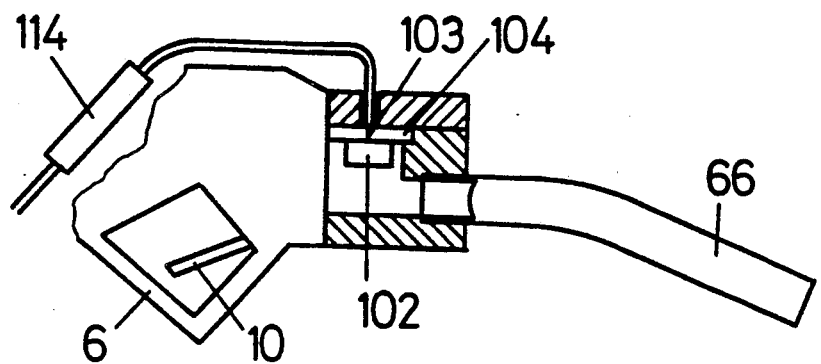
FIG. 5 is a cross-sectional view of a mounted detecting element.

The sensor 102 can be incorporated into the dispenser gun 6 either at the end of the discharge nozzle 66 as illustrated in FIG. 5 or, alternatively, into the dispenser gun 6 directly adjoining and located above an inner end of the discharge nozzle 66. A wire connection 104, 105, coming from the sensor, passes through the dispenser gun and runs with the hose 5 to the pedestal 38, 48, 58 and to the control system 70.

Figure 7:
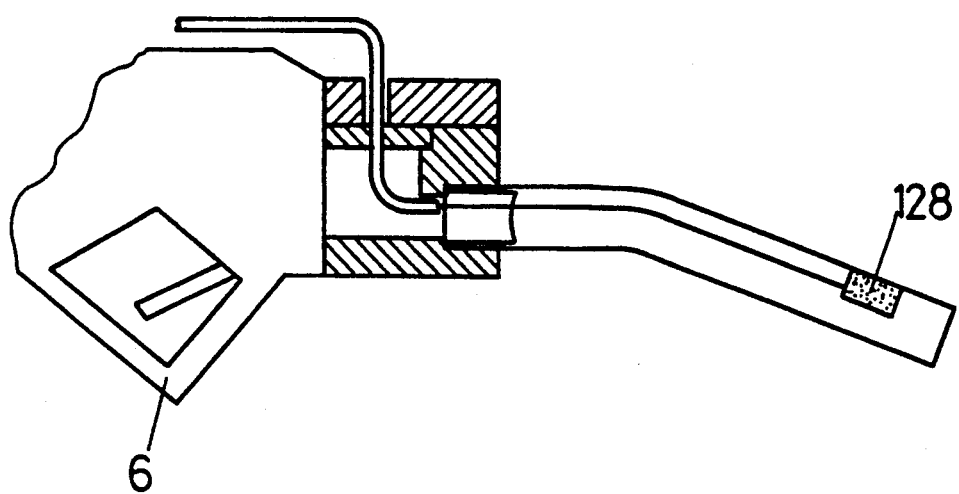
FIG. 7 is a cross-sectional view, similar to FIG. 5, of a further embodiment with a mounted detecting element.

The sensor 128 is preferably placed at the upper wall of either the dispenser nozzle, as illustrated in FIG. 7, or at the top of a hollow space inside of the dispenser gun 6 in order to better sense a gas evaporated from a liquid disposed lower. An indicator panel 114 (FIG. 5) can be placed on the top side of the dispenser gun 6 so as to allow an immediate reading while the dispenser gun 6 is placed in position.

Figure 4:
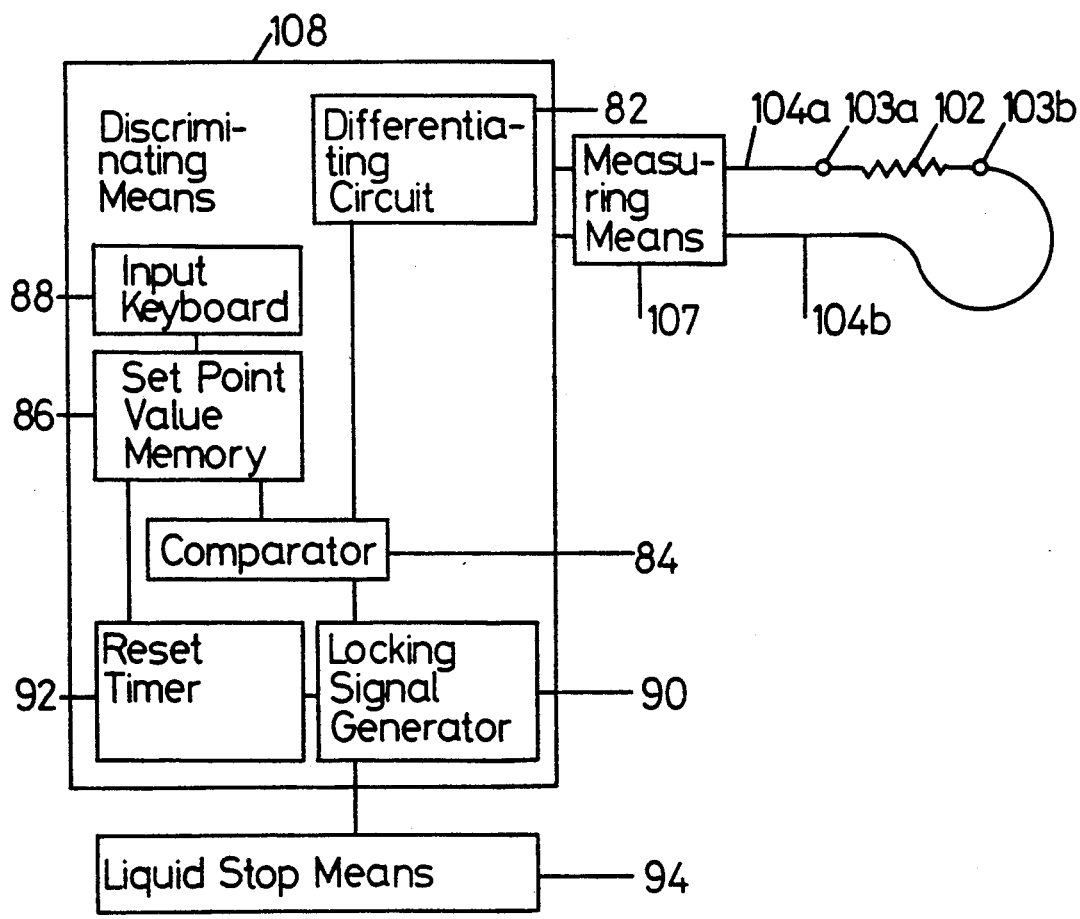
FIG. 4 is a block-circuit diagram illustrating the vaporized-liquid discriminator.

Such an increase of impedance is detected by a measuring means 107, according to FIG. 4, as an increase of the impedance between the connection lead wires 104a, 104b, each connected electrically to one of the two ends of the sensor 102. Upon increase of the impedance detected by the sensor and fed to the measuring means 107, the kind and quality of liquid or oil is determined by comparing the impedance increase rate per unit time with a preset reference changing rate of respective vaporized liquids or oils by the discriminating means 108 connected to the measuring means 107 as a circuit, or detecting an excess over a constant threshold value determined for vaporized oils or other fluids.

The discriminating means 108 includes a differentiating circuit 82 having an input connected to an output of the measuring means 107. The differentiating circuit 82 in turn has an output connected to an input of a comparator 84. A second input of the comparator 84 is connected to a set point value memory 86. The set point value memory 86 can be adjusted in its settings with a keyboard 88 electronically connected to the set point value memory 86. An output of the comparator 84 is connected to an input of a locking signal generator 90, and the locking signal generator in turn has an output connected to a liquid passage stop means 94. Upon finding, by way of the comparator, that the signal generated by the evaporated gas does not match the preset set point value, then the locking signal generator 90 will emit a signal via a connection to an input of a liquid stop means to stop a pumping of the fuel.

For easier operation, a reset means can be provided which resets the liquid stop means after a certain time in order to allow using the fuel dispenser for a further dispensing process. A reset timer 92 can be connected to the set point value memory in order to allow for placing a set point value for the reset time period into the set point value memory 86. The reset timer 92 can further be connected to the locking signal generator 90 either directly as shown in FIG. 4 or alternatively via the comparator 84.

Thus, the measurement can be performed based on a prior calibration of the sensor 2 for oils and liquids, based on the change of resistivity versus time for a certain time period, as well as based on a saturation value of resistance associated with a certain vaporized liquid.

According to the present invention, the evaporated liquid detecting element 102 has a structure where at least a pair of electrodes is bridged by a gas-sensing member consisting of resin material 102a, which includes a conductive substance. The molecules of a vaporized liquid from an oil or liquid enter the gas-sensing member surrounding the particles of the conductive substance and they interfere with the electrical conductivity of the evaporated liquid detecting element 102. Consequently, an impedance value, determined between the electrodes, increases and such impedance change is detected by a measuring means 107. Since an oil, having a higher volatility, is vaporized within a shorter period of time, the impedance value increases quicker. Thus, the kind of oil can be discriminated by comparing the changing rate per time for an oil with a preset changing rate per time for different kinds of oil in a discriminating means, or by providing a constant threshold value or otherwise. An electronic memory element 86 is employed in storing the setpoint values for the changing rate or, respectively, the saturation of the various fuels to which such pump can be adapted.

Since the detecting element 102 of the present invention detects the kind of molecules of vaporized oil, the oil molecules, passing to the conductive material in the gas-sensing part, are vaporized and an impedance value of the vaporized-liquid detecting element is reset to its initial value.

The present invention discloses a vaporized-liquid detecting element and a vaporized-liquid discriminating apparatus which utilize the vaporized-liquid detecting element. The detecting element and the discriminating means 108 are capable of sensing a kind of fuel or oil such as gasoline, light oil, or kerosene, in a distinguished and discriminating way within a short period of time and can be quickly reset for reuse. Therefore, a means is provided which prevents the feeding of erroneous kinds of oil and gas at a gas-service station, thereby contributing to the prevention of disasters and dangers while simultaneously assuring a safe operation.

In particular, the evaporated residual liquid to be resupplied to a storage tank can be quickly detected and a supply of the wrong fuel can be prevented with the liquid supply apparatus attached at the end part of a liquid supply line. A detecting element is provided which detects liquid from a storage tank to be replenished based on vaporized gases of residual fuel in the storage tank 15 and where additional supply is provided through a supply line associated with the detecting element 102. A discriminator is connected to the detecting element 102 for discriminating the information obtained from such detecting element versus set points and the discriminator generates a lock signal. A locking means connected to the discriminator can suspend and interrupt a supply of liquid based on the signal generated in the discriminator. Consequently, the present invention provides a safety device which is capable of both preventing dangers and disasters while, at the same time, saving labor costs and assuring a safe operation of hazardous fuels.

It will be understood that each of the elements described above, or two or more together, may also find a useful application in other types of liquid supply systems differing from the types described above.

While the invention has been illustrated and described as embodied in the context of the supply of vaporizable liquids for industrial use, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims.

We claim:

1. A liquid dispensing apparatus comprising
a liquid supply line having an input and having an output end;
a dispenser gun attached to the output end of the liquid supply line;
a detecting element including a measuring means having an impedance change depending on a surrounding evaporated gas and attached to the dispenser gun for detecting the kind of liquid to be supplied from a gas evaporated from residual liquid surrounding a location which requires additional supply, said detecting element furnishing a sensor signal corresponding to the evaporated gas;
a discriminator connected to the detecting element for discriminating the sensor signal obtained from said detecting element and for generating a lock signal depending on distinction based on the kind of gas derived from evaporated liquid surrounding the location; and
a locking means connected electronically to the discriminator and actuated by said lock signal of the discriminator for interrupting dispensing of liquid depending on the lock signal furnished by the discriminator, further comprising
an outlet tube disposed at the output end of the dispenser gun, wherein the detecting element is disposed in the outlet tube for a liquid near the output end of the liquid supply line, and wherein the detecting element is covered with a protective film, which is permeable to gas but impermeable to liquid.

2. A liquid dispensing apparatus comprising
a liquid supply line having an input and having an output end;
a dispenser gun attached to the output end of the liquid supply line;
a detecting element including a measuring means having an impedance change depending on a surrounding evaporated gas and attached to the dispenser gun for detecting the kind of liquid to be supplied from a gas evaporated from residual liquid surrounding a location which requires additional supply, said detecting element furnishing a sensor signal corresponding to the evaporated gas at an output;
a discriminator connected to the detecting element for discriminating the sensor signal obtained from said detecting element and for generating an electronic lock signal depending on distinction based on the kind of gas derived from evaporated liquid surrounding the location; and
a locking means having an electronic input connected electronically to the discriminator and actuated by said lock signal of the discriminator for interrupting dispensing of liquid depending on the lock signal furnished by the discriminator, wherein
the discriminator is an electronic circuit which generates the electronic lock signal for controlling the operation of the locking means including
a differentiating circuit having an input connected to an output of the detecting element;
a comparator having a first input connected to an output of the differentiating circuit and having a second input;
a set point value memory having an input and having an output connected to a second input of the comparator;
a lock signal generator having an input connected to the comparator and having an output connected to an electronic input of the locking means.

3. The liquid dispensing apparatus according to claim 2, further comprising
an input keyboard connected to the set point value memory for adjusting set point values stored in the set point value memory;
a reset timer having an input connected to the output of the set point value memory for receiving a set point value from the memory and having an output connected to the lock signal generator;
a display mounted to the top of the dispenser gun as disposed in a filling position and connected to the comparator.

4. A liquid dispensing apparatus comprising
a liquid supply line having an input and having an output end;
a dispenser gun attached to the output end of the liquid supply line;

a detecting element including a measuring means having an impedance change depending on a surrounding evaporated gas and attached to the dispenser gun for detecting the kind of liquid to be supplied from a gas evaporated from residual liquid surrounding a location which requires additional supply, said detecting element furnishing a sensor signal corresponding to the evaporated gas;

a discriminator connected to the detecting element for discriminating the sensor signal obtained from said detecting element and for generating a lock signal depending on distinction based on the kind of gas derived from evaporated liquid surrounding the location; and a locking means connected electronically to the discriminator and actuated by said lock signal of the discriminator for interrupting dispensing of liquid depending on the lock signal furnished by the discriminator, wherein the detecting element is formed by a first electrode, a second electrode, a gas-sensing member disposed between the first and the second electrode, said gas-sensing member is formed of resin material including a conductive substance, and which conductive substance changes its impedance upon being placed in contact with a vaporized gas of a liquid to be detected, wherein the detecting element is provided by a measuring means having an impedance change depending on the surrounding vaporized gas and wherein the discriminator is connected to and adapted to the measuring means for allowing to distinguish liquids to be detected based on their vapors, wherein the detecting element is an elongated structure disposed aligned with the direction of output wires of the detecting element;

a socket disposed between the gas sensing member and ends of respective output wires for allowing a quick connection of the gas sensing member to the socket.

* * * * *